United States Patent [19]

Ueno et al.

[11] Patent Number: 4,916,233

[45] Date of Patent: Apr. 10, 1990

[54] METHOD FOR PRODUCTION OF 4-METHYL-5-(2-AMINOETHYL)-THIOMETHYL)-IMIDAZOLE

[75] Inventors: Tsunemasa Ueno, Kawasaki; Koichi Yamamoto, Tokyo; Masao Kitano, Kamakura; Yutaka Morimoto, Yokohama, all of Japan

[73] Assignee: Nippon Shokubai Kagaku Kogyo Co., Ltd., Osaka, Japan

[21] Appl. No.: 342,798

[22] Filed: Apr. 25, 1989

[30] Foreign Application Priority Data

| Apr. 26, 1988 | [JP] | Japan | 63-101243 |
| May 27, 1988 | [JP] | Japan | 63-128193 |
| May 27, 1988 | [JP] | Japan | 63-128194 |
| May 31, 1988 | [JP] | Japan | 63-131497 |
| Jun. 1, 1988 | [JP] | Japan | 63-132832 |
| Jun. 1, 1988 | [JP] | Japan | 63-132833 |
| Jun. 14, 1988 | [JP] | Japan | 63-144688 |
| Sep. 22, 1988 | [JP] | Japan | 63-236327 |
| Sep. 28, 1988 | [JP] | Japan | 63-240799 |
| Sep. 30, 1988 | [JP] | Japan | 63-243800 |

[51] Int. Cl.$^4$ ............................ C07D 233/64
[52] U.S. Cl. ................................. 548/342
[58] Field of Search ......................... 548/342

[56] References Cited

U.S. PATENT DOCUMENTS

| 3,950,333 | 4/1976 | Durant et al. | 548/342 X |
| 4,049,672 | 9/1977 | Durant et al. | 548/342 |
| 4,189,592 | 2/1980 | Halbritter | 548/342 |

*Primary Examiner*—Richard A. Schwartz
*Attorney, Agent, or Firm*—Burns, Doane, Swecker & Mathis

[57] ABSTRACT

4-Methyl-5-[(2-aminoethyl)-thiomethyl]-imidazole can be effectively produced by causing 4-methylimidazole or a salt thereof to react with at least one member selected from the group consisting of (a) a formaldehyde adduct of cysteamine, (b) 2-aminoethanethiol sulfuric acid and formaldehyde or a formaldehyde oligomer, and (c) thiazolidine or a salt thereof, in the presence of a mineral acid, removing a portion of reaction liquid out of the reaction system while maintaining molar concentration of 4-methyl-5-[(2-aminoethyl)-thiomethyl]-imidazole in the reaction system not exceeding 70 mol % based on total mol numbers of 4-methylimidazole and 4-methyl-5-[(2-aminoethyl)-thiomethyl]-imidazole, then separating a liquid containing 4-methyl-5-[(2-aminoethyl)-thiomethyl]-imidazole from the removed portion of reaction liquid, and recycling the remainder into the reaction system.

11 Claims, 3 Drawing Sheets

METHOD FOR PRODUCTION OF 4-METHYL-5-(2-AMINOETHYL)-THIOMETHYL)-IMIDAZOLE

BACKGROUND OF THE INVENTION

1. Field of the Invention

This invention relates to a method for the production of 4-methyl-5-[(2-aminoethyl)-thiomethyl]-imidazole.

2. Description of the Prior Art

4-Methyl-5-[(2-aminoethyl)-thiomethyl]-imidazole is a compound which has important utility as an intermediate for the synthesis of cimetidine known as a histamine $H_2$ acceptor antagonist.

As means of producing a 4-methyl-5-[(2-aminoethyl)-thiomethyl]-imidazole, (1) a method which comprises causing hydroxymethylimidazole to react with cysteamine in concentrated hydrochloric acid (U.S. Pat. Nos. 3,950,333 and 4,049,672) and (2) a method which comprises causing 4-methylimidazole in concentrated hydrochloric acid to react with cysteamine an formaldehyde or thiazolidine (U.S. Pat. No. 4,189,592) have been known to the art.

The former method, however, has a disadvantage that 4-methyl-5-[(2-aminoethyl)-thiomethyl]-imidazole to be produced thereby is expensive because 4-methyl-5-hydroxymethyl imidazole is used as a starting material therefor. This is because the 4-methyl-5-hydroxmethyl imidazole is produced by a method which comprises causing 4-methylimidazole to react with formaldehyde in hydrochloric acid or a method which comprises reducing a 4-methylimidazole-5-carboxylic ester and either of these methods entails a complicated operation and affords the product in a low yield. As an improved version of the former method which comprises cauasing 4-methyl-5-hydroxylmethyl imidazole to react with cysteamine in concentrated hydrochloric acid, the latter method obtains 4-methyl-5-[(2-aminoethyl)-thiomethyl]-imidazole by one step from 4-methylimidazole.

Figure 3:
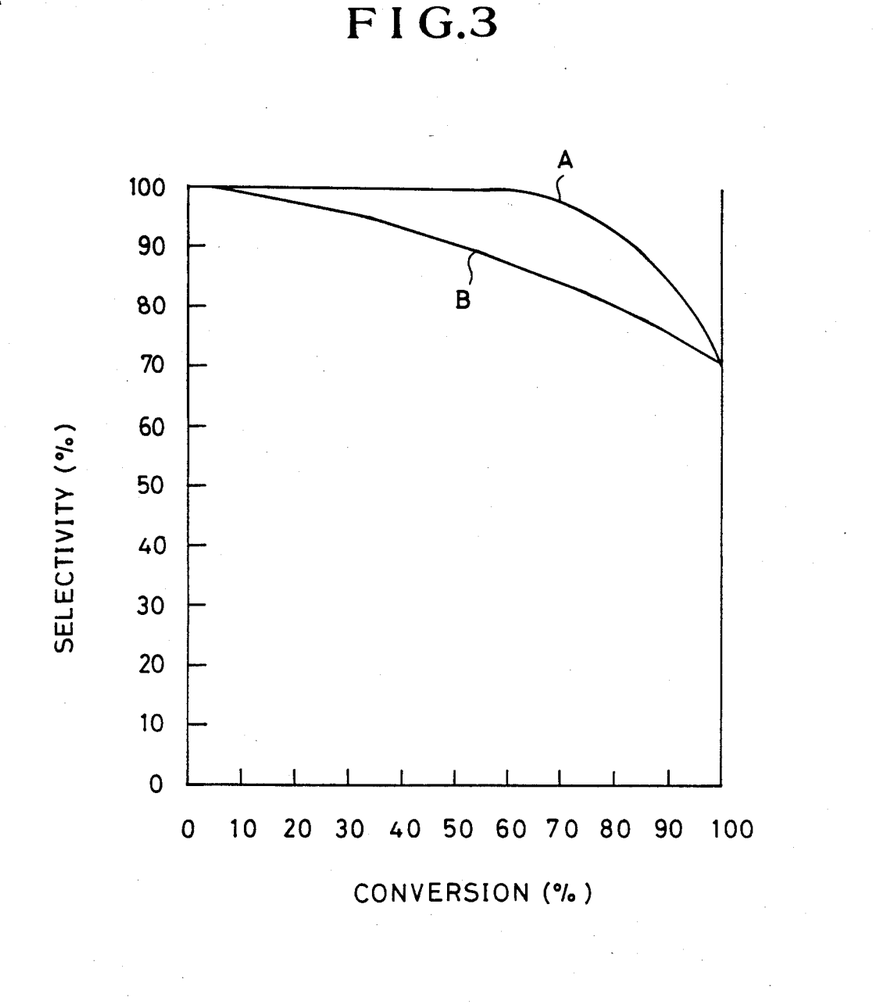
FIG. 3 is a graph illustrating relationship between conversion and selectivity in the method of the present invention and that of other method.

When we have analyzed on the simultaneous reaction among 4-methylimidazole, cysteamine, and formaldehyde in detail, the relationship between conversion of 4-methylimidazole and selectivity of 4-methyl-5-[(2-aminoethyl)-thiomethyl]-imidazole has been obtained as shown in the curve B in FIG. 3, indicating that selectivity was decreased owing to generation of the subsequent reactio at the beginning of the reaction. For this reason, when the product was isolated from the reaction liquid, it was necessary to remove the by-product otherwise removal of the unaltered raw materials. Accordingly, we have found that such reaction has disadvantages that effectivity of formation is low as well as re-use of the unaltered raw material is substantially impossible.

An object of this invention is therefore, to provide a novel method for the production of a 4-methyl-5-[(2-aminoethyl)-thiomethyl]-imidazole.

Another object of this invention is to provide a method for producing a 4-methyl-5-[(2-aminoethyl)-thiomethyl]-imidazole of high purity from 4-methylimidazole in a high yield.

SUMMARY OF THE INVENTION

These objects are accomplished by a method for the production of 4-methyl-5-[(2-aminoethyl)-thiomethyl]-imidazole comprising causing 4-methylimidazole or a salt there of to react with at least one member selected from the group consisting of (a) a formaldehyde adduct of cysteamine (b) 2-aminoethenethiol sulfuric acid and formaldehyde or a formaldehyde oligomer, and (c) thiazolidine or a salt thereof, in the presence of a mineral acid, removing a portion of a reaction liquid out of the reaction system which maintaining molar concentration of 4-methyl-5-[(2-aminoethyl)-thiomethyl]-imidazole in the reaction system not exceeding 70 mol % based on total mol numbers of 4-methylimidazole and 4-methyl-5-[(2-aminoethyl)-thiomethyl]-imidazole, then separating a liquid containing 4-methyl-5-[(2-aminoethyl)-thiomethyl]-imidazole from the reaction liquid, and recycling a remainder into the reaction system.

These objects are also accomplished by a method for the production of a 4-methyl-5-[(2-aminoethyl)-thiomethyl]-imidazole by the reaction of 4-methylimidazole or a salt thereof with (a) a formaldehyde adduct of cysteamine (b) 2-aminoethanethiol sulfuric acid and formaldehyde or a formaldehyde oligomer in the presence of a mineral acid.

These objects are also accomplished by a method for the production of a 4-methyl-5-[(2-aminoethyl)-thiomethyl]-imidazole by the 5 reaction of 4-methylimidazole or a salt thereof with thiozolidine or a salt thereof in the presence of sulfric acid.

The present invention, which involves removing the reaction liquid out of the reaction system while maintaining molar concentration of 4-methyl-5-[(2-aminoethyl)-thiomethyl]-imidazole in the reaction system not exceeding 70 mol % based on total mol numbers of 4-methylimidazole and 4-methyl-5-[(2-aminoethyl)-thiomethyl]-imidazole can easily produce a high quality of reaction product, 4-methyl-5-[(2-aminoethyl)-thiomethyl]-imidazole, with substantial no formation of by-product. Separation of unreacted raw materials from the reaction liquid and circulation thereof make them convert into the reaction product substantially quantitatively. Accordingly, the present invention can provide a method which can continuously carry out a process involving recovery and reuse, which method can be considered to be commercially available.

EXPLANATION OF THE PREFERRED EMBODIMENT

In accordance with the present invention, the 4-methyl-5-[(2-aminoethyl)-thiomethyl]-imidazole is obtained by causing 4-methylimidazole or a salt thereof to react with (a) a formaldehyde adduct of cysteamine or (b) 2-aminoethanthiol suolfuric acid acid and formaldehyde or a formaldehyde oligomer in the presence of a mineral acid, or with (c) thiazolidine or a salt thereof in the presence of sulfuric acid.

In accordance with another aspect of the present invention 4-methyl-5-[(2-aminoethyl)-thiomethyl]-imidazole can be produced by causing 4-methylimidazole or a salt thereof to react with at least one member selected from the group consisting of (a) a formaldehyde adduct of cysteamine, (b) 2-aminoethanethiol sulfuric acid and formaldehyde or a formaldehyde oligomer, and (c) thiazolidine or a salt thereof, in the presence of a mineral acid, removing a portion of a reaction liquid out of the reaction system while maintaining molar concentration of 4-methyl-5-[(2-aminoethyl)-thiomethyl]-imidazole in the reaction system not exceeding 70 mol % based on total mol numbers of 4-methyl-5-[(2-aminoethyl)-thiomethyl]-imidazole, then separating a liquid containing 4-methyl-5-[(2-aminoethyl)-thiomethyl]-imidazole from the reaction liquid, and recycling a remainder into the reaction system.

The mineral acids which are usable for this invention include hydrohalogenous acids such as hydrochloric acid and hydrobromic acid, sulfuric acid, and phosporic acid. Generally, the mineral acid is used in the form of an aqueous solution containing the mineral acid in a concentration in the range of 10 to 70% by weight, preferably 20 to 60% by weight. The mineral acid is used in an amount in the range of 2 to 8 mols, preferably for the sake of economy and productivity in the range of 2 to 5 mols, per mol of 4-methylimidazole as a raw material. The 4-methylimidazole is used in the form of a free base or in the form of a salt neutralized with such a mineral acid as hydrochloric acid, hyrobromic acid, sulfuric acid, or phosphoric acid.

The formaldehyde or formaldehyde oligomer is used in the form of an aqueous solution containing formaldehyde in a concentration in the range of 30 to 40% by weight or as a paraformaldehyde or 1,3,5-trioxane, for example.

The 2-aminoethanethiol sulfuric acid can be produced by any of the well-known methods such as, for example, (A) a method which comprises causing a halogenoethylamine to react with a thiosulfuric acid, separating an inorganic salt from the resultant reaction solution by filtration, concentrating and drying to hardness the filtrate, further removing the persistant inorganic salt from the dried filtrate with a mixed solvent comprising a lower alcohol such as methanol or ethanol with water, and recrystallizing the remainder or (B) a method which comprises causing aminoethyl sulfuric acid or ehtyleneimine to react with a thiosulfuric acid in the presence of an alkaline catalyst, separating an inorganic salt from the resultant reaction solution by filtration, concentrating and drying to hardness the filtrate, further removing the persistent inorganic salt from the dried concentrate with a mixed solvent comprising a lower alcohol with water, and concentrating and drying to hardness the remainder.

It can be produced by (C) a method which has been developed for the first time by us and which comprises causing a hydrogen halide of a halogenoethylamine or an aminoethyl sulfuric ester to react with thiosulfuric acid in the presence of an alkaline catalyst and subjecting the reaction solution containing 2-aminoethanethiol sulfuric acid to electrodialysis thereby removing an inorganic salt from the reaction solution. This method is advantageous from the commercial point of view because the purification of 2-aminoethanthiol sulfuric acid can be carried out very simply without entailing any complicate operation. Though this method generally uses water as the solvent, it may use a mixed solvent comprising an alcoholic solvetn and water for the sake of the solution of raw materials used in the reaction. The alcoholic solvents which are usable herein include methanol, ehanol, isopropanol, and butanol, for example. The reaction (C) is carried out by first dissolving the starting materials in the solvent and then heating the resultant solution at a temperature in the range of 50° to the boiling point of the solvent to be used. For the sake of the reaction rate, the reaction temperature is preferable to be as high as permissible. This reaction, when necessary, may be carried out under application of pressure. Though the reaction time is variable with the reaction temperature and the concentration of the reaction solution, it is generally in the range of 1 to 40 hours, preferably 5 to 30 hours. The amount of the thiosulfuric acid to be used is in the range of 0.5 to 2mols, preferably 0.9 to 1.1 mols, per mol of the hydrogen halide of the halogenoethylamine or aminoethyl sulfuric ester. The device for electrodialysis to be used in the method is similar to that which will be described hereinafter.

Thiasolidine to be used for the method of the present invention is used in the form of free base or a mineral acid salt.

The adduct of cysteamine with formaldehyde to be used for the method of the present invention can be easily produced by mixing cysteamine with formaldehyde in equimolecular proportion at a normal room temperature. The cysteamine is used in free base or a mineral salt form. Formaldehyde used for the method of the present invention is used as an aqueous solution containing 30 to 40% by weight of formaldehyde or paraformaldehyde. The 4-methylimidazole is used in the form of a free base or in the form of a salt neutralized with such a mineral acid as hydrochloric acid, hydrobromic acid, sulfuric acid, or phosphoric acid.

The molar ratio of 4-methylimidazole, 2-aminoethanethiol sulfuric acid, and formaldehyde for the method of this invention is in the range of 1:09–1.7:0-.9–1.1 preferably approximately 1:1.

The molar ratio of 4-methylimidazole to thiazolidine or its salt is in the range of 1:0.9–1.1, preferably approximately 1:1. The molar ratio of 4-methylimidazole to a formaldehyde adduct of cysteamine is in the range of 1:0.9–1.1, preferably approximately 1:1.

The reaction is carried out at a temperature in the range of 100° to 180° C., preferably 120° to 150° C. The retention of the reaction solution generally falls in the range of 30 minutes to 10 hours, preferably 1 to 5 hours, though it is variable with the amount of the mineral acid to be used, the concentration of the mineral acid, and the reaction temperature.

The 4-methyl-5-[(2-aminoethyl)-thiomethyl]-imidazole to be formed by the method of this invention is obtained in the form of a mineral acid salt. The isolation of the reaction product is attained by removing the excess acid by neutralization or distillation, concentrating and drying to hardness the reaction solution under a vacuum, and recrystallizing the residue from a lower alcohol such as methanol or ethanol or from acetic acid.

Otherwise, the isolation may be attained by washing hot the reaction solution with an alochol such as 1-propanol or 2-butanol thereby removing the unaltered reactants therefrom. Where the reaction product is to be isolated in the form of a free base, this isolation can be easily accomplished by neutralizing the reaction solution with an alkali and extrating the resultant base with a solvent.

The reaction of the 4-methylimidazole or a salt thereof, with (a) a formaldehyde adduct or (b) 2-aminoethanethiol sulfuric acid, and the formaldehyde in the reaction system of a mineral acid or with (c) thiazolidine or a salt thereof in the reaction system of sulfuric acid as contemplated by the present invention is preferably fulfilled by mixing 4-methylimidazole, (a) formaldehyde adduct of cysteamine or (b) 2-aminoethanethiol sulfuric acid, and an aqueous formaldehyde solution or 4-methylimidazole and (b) thiazolidine or a salt thereof in a prescribed ratio, continuously supplying the resultant mixture into an acid, and heating the reaction mixture to the aforementioned temperature.

As means for separating the product, i.e. a 4-methyl-5-[(2-aminoethyl)-thiomethyl]-imidazole, and the unaltered reactants from the reaction solution withdrawn from the reaction system of the present invention, the method of column separation and the method of electrodialysis may be mentioned. The method of electrodialysis proves to be particularly preferable.

The electrodialytic device to be used in the present invention is not extraordinary. Specifically, it comprises an array of a multiplicity of alternate cation-exchange membranes and anion-exchange membranes and a pair of electrodes disposed one each at the opposite ends of the array. In the compartments having an anion-exchange membrane on the anode side and a cation-exchange membrane on the cathode side, the cations produced by the ionization move toward the anodes, permeate through the cation-exchange membranes, and pass into the adjoining compartments, wherein they are prevented from dialysis by the anion-exchange membranes. When proper exchange membranes such as, for example, those made by Asahi Chemical Industry Co., Ltd. and marketed under product code of "AC-110" are used in the present electrodialysis, the materials having smaller molecular weights than the product are allowed to pass through the cation-exchange membranes and the 4-methyl-5-[(2-aminoethyl)-thiomethyl]-imidazole having a larger molecular weight is prevented from permeating the membranes, with the result that the separation of the product from the other substances is accomplished thus easily.

The inner liquid containing the reaction product 4-methyl-5-[(2-aminoethyl)-thiomethyl]-imidazole is in the next step as it is as desired. Alternatively it may be used in crystal form by concentrating the inner liquid and then crystallizing it with such a poor solvent as methanol, ethanol, n-propanol or isopropanol.

The outer liquid containing the raw materials may be recycled to the reaction system either in its unaltered form or after it has been concentrated or diluted to a suitable concentration.

In the present invention, the fact that the molar concentration of the 4-methyl-5-[(2-aminoethyl)-thiomethyl]-imidazole in the reaction system is kept at or below 70 mol %, preferably in the range of 60 to 40 mol %, based on the total number of mols of 4-methyl-5-[(2-aminoethyl)-thiomethyl]-imidazole is aimed at substantially preventing the continuous reaction from giving rise to a by-product. By this continuous reaction, therefore, the 4-methyl-5-[(2-aminoethyl)-thiomethyl]-imidazole, i.e. the reaction product to be obtained has high quality. The unaltered reactants can be converted substantially quantitatively into the reaction product by separating the unaltedred reactants from the reaction solution and recycling the recovered unaltered reactants to the reaction system.

Such continuous method is carried out as follows: In an apparatus illustrated in FIG. 1, formaldehyde or oligomer thereof, 4-methylimidazole, and 2-aminoethanethiol sulfuric acid are respectively supplied through conduits 1,2, and 3 into a mixing tank 4 and they are thoroughly mixed. The mixture is supplied from the mixing tank 4 into a reactor 6 via a conduit 5. The reaction solution is continuously withdrawn from the reactor 6 via a conduit 7 and then allowed to cool. The cooled liquid is sent to a separator, e.g. an electrodialytic device 10 via a conduit 9. When water is supplied through a conduit 11 as an outer liquid an aqueous solution of 4-methyl-5-[(2-aminoethyl)-thiomethyl]-imidazole is obtained from a conduit 12. As soon as the deposited precipitate is filtered and dried, a crystal of 4-methyl-5-[(2-aminoethyl)-thiomethyl]-imidazole can be obtained as a form of salt. The outer liquid obtained in the electrodialysis is withdrawn through a conduit 13 and supplied to a concentrater 14 thereby concentrating it, the liquid is returned to the reactor 6. In the case of using thiazolidine or salt thereof as the raw material, it is supplied to the mixing tank 4 through the conduit 1 or 3 and optionally the mineral acid is supplied thereto through anyone of the remaining conduit. In the case of using the formaldehyde adduct of cysteamine as the raw material, as shown in FIG. 2, cysteamine and formaldehyde are supplied through conduits 1 and 3, respectively to a mixing tank 4 to form the adduct and then supplied to a reactor 6 through a conduit 4, while supplying 4-methylimidazole to the reactor 6 through a conduit 2a.

Now, the present invention will be described more specifically below with reference to working examples, which are purely illustrative and not limitative of the present invention.

REFERENTIAL EXAMPLE 1

In 100.0 g of purified water, 16.3 g (0.1 mol) of sodium thiosulfuric acid was dissolved. The resultant solution was kept below 30° C. and 23.2 g (0.1 mol) of an aqueous 50% 2-chloroethylamine hydrohloride solution was added dropwise thereto. The resultant mixture was adjusted to pH 9.0 by addition of sodium hydroxide. Then, it was gradually heated to a reflux temperature and then refluxed and stirred for 15 hours. The reaction solution consequently obtained was treated with an electrodialytic device using ion-exchange membranes (produced by Asahi Chemical Industry Co., Ltd.) An aqueous 5% sodium sulfuric acid solution was used as an electrode liquid and an aqueous 5% sodium chloride solution as a concentration liquid. By concentrating and then crystallizing the demineralized liquid by electrodialysis, there were obtained 14.2 g (yield 90%) of white crystals of 2-aminoethanethiol sulfuric acid. The filtrate was recycled to the reaction system of the step for demineralization of the reacation solution.

REFERENTIAL EXAMPLE 2

In 100.0 of purified water, 19.0 g (0.1 mol) of potassium thiosulfuric acid was dissolved. The resultant aqueous solution was kept below 30° C. and 14.1 g (0.1 mol) of 2-aminoethyl sulfuric acid was added thereto and dissolved therein. The resultant mixture was adjusted to pH 8.0 by addition of potassium hydroxide. Then, this mixture was slowly heated to a reflux temperature and then refluxed and stirred for 20 hours. The reaction solution consequently obtained was treated with an electrodialytic device using ion-exchange membranes (produced by Asahi Chemical Industry Co., Ltd.). An aqueous 5% sodium sulfuric acid solutioin was used as an electrode liquid and an aqueous 5% potassium sulfuric acid as a concentration liquid.

The demineralized liquid obtained by the electrodialysis was concentrated and crystallized, to obtain 14.6 g (yield 93%) of white cyrstals of 2-aminoethanethiol sulfuric acid. The filtrate was recycled to the reaction system or to the step of demineralization of the reaction solution.

EXAMPLE 1

In 30.4 g of an aqueous 36 wt % hydrogen chloride solution, 8,7 g of 4-methylimidazole 96% in purity, 15.7 g of 2-aminoethanethiol sulfuric acid, and 8.1 g of an aqueous 37 wt % formaldehyde solution were dissolved as kept cooled below 30° C. In a closed glass-lined autoclave, the resultant mixture was stirred and heated at 140° C. for 20 hours. To the resultant reaction solution, 600 g of an aqueous 20 wt % sodium hydroxide solution kept below 30° C. was added. Then, the resultant mixture was concentrated and dried to hardness under a vacuum. The residue and 65.0 g of ethanol added thereto were refluxed for 1 hour. Then, the residue was hot filtered. The filtrate was further cooled and the precipitate consequently produced was separated by filtration. The filtrate was dried under a vacuum, to obtain 17.6 g (82.1% yield) of white crystals of 4-methyl-5-[(2-aminoethyl)-thiomethyl]-imidazole hydrochloride. The melting point of this product was 186° to 189° C.

EXAMPLE 2

In 392 g of an aqueous 50 wt % sulfuric acid solution, 8.6 g of 4-methylimidazole 97.6% in purity, 15.7 g of 2-aminoethanethiol sulfuric acid, and 3.8 g of 80 wt % paraformaldehyde were dissolved as kept cooled below 30° C. The resultant mixture was placed in a closed glass-lined autoclave and stirred and heated therein at 120° C. for 10 hours and then at 140° C. for 10 hours. To the resultant reactio solution, 40.0 g of an aqueous 48 wt % sodium hydroxide solution was thoroughly stirred and then left standing at rest for 30 minutes. The upper layer alone was taken out. The oil substance was dissolved in 20.3 g of an aqueous 36 wt % hydrogen chloride solution. The resultant solution was concentrated and dried to hardness and then leached in 88.0 g of 1-propyl alcohol at the boiling point for one hour. The decoction was hot filtered. By drying the residue, there were obtained 18.6 g (84.2% in yield) of white crystals of 4-methyl-5-[(2-aminoethyl)-thiomethyl]-imidazole hydrochloride. The melting point of this product was 184° to 186° C.

EXAMPLE 3

In 392 g of an aqueous 50 wt % sulfuric acid solution, 82 g of 4-methylimidazole, 157 g of 2-aminoethanethiol sulfuric acid, and 81 g of an aqueous 37% formalin solution were dissolved. In an autoclave, the resultant mixture was heated and stirred at 140° C. for 2 hours. In 712 g of the resultant reaction solution, there were contained 135 g of 4-methyl-5-[(2-aminoethyl)-thiomethyl]-imidazole sulfuric acid, 65 g of ½ sulfuric acid of 4-methylimidazole, and other unaltered reactants and sulfuric acid, indicating that the conversion of 4-methylimidazole was 50%.

Then, the reaction solution as an inner liquid and 600 g of water as an outer liquid were treated with an electrolytic device using ion-exchange membranes (produced by Asahi Chemical Industry Co., Ltd. and marketed under product code of "AC-110"), with an aqueous 50% sodium sulfuric acid solution used as an electrode liquid. During the course of the electrodialysis, the outer liquid was displaced with 600 g of water to continue the electrodialysis further.

Finally, 253 g of a liquid containing 81 g of 4-methyl-5-[(2-aminoethyl)-thiomethyl]-imidazole sulfuric acid and 172 g of water was obtained as the inner liquid. At the same time, 1,650 g of a liquid containing 54 g of 4-methyl-5-[(2-aminoethyl)-thiomethyl]-imidazole sulfuric acid, 65 g of ½ sulfuric acid of 4-methylimidazole, and other unaltered reactants and sulfuric acid was obtained as the outer liquid.

The inner liquid thus obtained was concentrated under a vacuum and thrown into 1-propyl alcohol. The crystals consequently precipitated were separated by filtration and dried, to produce 73 g of white crystals of 4-methyl-5-[(2-aminoethyl)-thiomethyl]-imidazole sulfuric acid.

EXAMPLE 4

The outer liquid obtained in Example 3 was concentrated under a vacuum to 610 g. In an autoclave, the concentrate and 24.6 g of 4-methylimidazole, 47.1 g of 2-aminoethanethiol sulfuric acid, and 24.3 g of an aqueous 37% formalin solution added thereto were heated for reactio at 140° C. for 1 hour and 30 minutes. The resultant reaction solution contained 134 g of 4-methyl-5-[(2-aminoethyl)-thiomethyl]-imidazole sulfuric acid, 65 g of ½ sulfuric acid of 4-methylimidazole, other naltered reactants, and sulfuric acid, representing the same composition as the reaction solution of the first cycle of reaction. When this reaction solution was subjected to electrodialysis in the same manner as in Example 3, there was obtained 255 g of a liquid containing 80 g of 4-methyl-5-[(2-aminoethyl)-thiomethyl]-imidazole sulfuric acid and the balance of water. The outer liquid was concentrated under a vacuum and then recycled to the next cycle of reaction.

EXAMPLE 5

Figure 1:
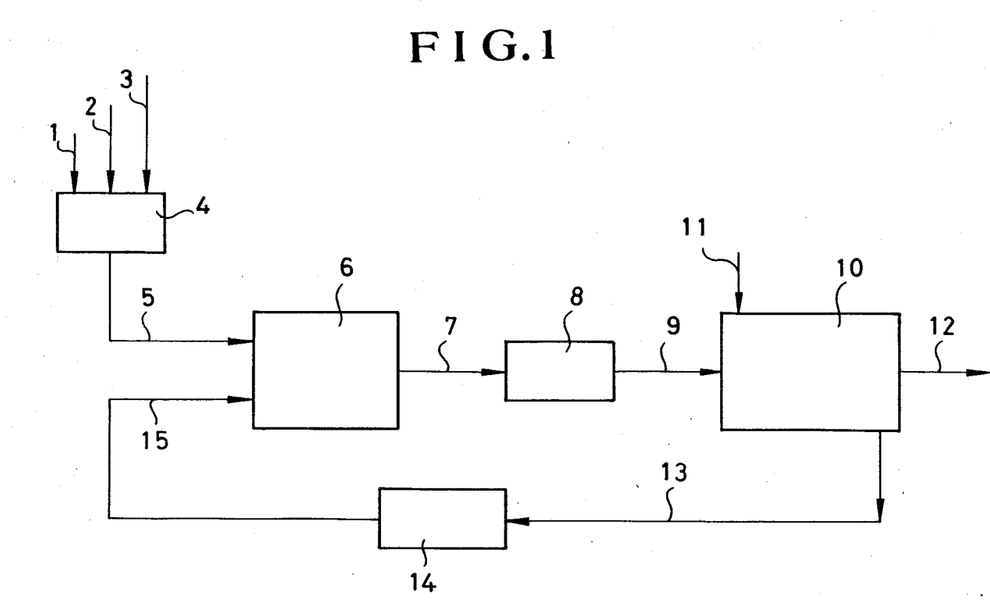
FIG. 1 is a flow sheet illustraitng one embodiment of the present invention.
Figure 2:
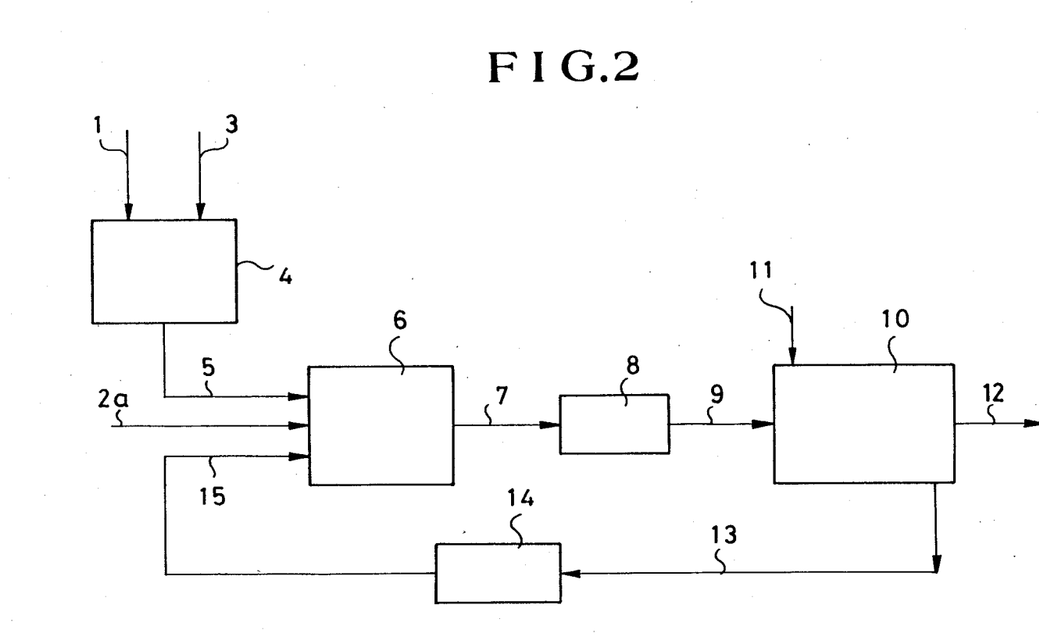
FIG. 2 is a flow sheet illustrating another embodiment of the present invention.

In an apparatus constructed as illustrated in FIG. 1, an aqueous 37 wt % formldehyde solution was supplied at a flow rate of 20.2 g/hr through a conduit 1, 4-methylimidazole at a flow rate of 20.4 g/hr through a conduit 2, and 2-aminoethanethiol sulfuric acid at a flow rate of 39.1 g/hr through a conduit 3 respectively into a mixing tank 4. The resultant mixture was supplied at a flow rate of 79.7 g/hr from the mixing tank 4 through a conduit 5 to a reactor 6 kept at 140° C. The retention time of the reaction solution in the reactor 6 was 2 hours. From the reactor 6, the resultant reaction solution was continuously withdrawn at a flow rate of 712 g/hr throughy a conduit 7. This reaction solution contained 18.9% by weight of 4-methyl-5-[(2-aminoethyl)-thiomethyl]-imidazole sulfuric acid, 9.2% by weight of ½ sulfuric acid of 4-methylimidazole, and the balance of unaltered reactants and sulfuric acid, indicating that the conversion of 4-methylimidazole was 50%. This reaction solution was placed in a condenser 8 and cooled therein to below 50° C. and was supplied through a conduit 9 as an inner liquid to an electrodialytic device using ion-exchange membranes (produced by Asahi Chemical Industry Co., Ltd. and marketed under product code of "AC-110"), with an aqueous 5% sodium sulfuric acid solution used as an electrode liquid. Through a conduit 11, water was supplied as an outer liquid to the electrodialytic device at a flow rate of 1,000 g/hr. Through a conduit 12, an aqueous 29.9 wt % 4-methyl-5-[(2-aminoethyl)-thiomethyl]-imidazole [(2-aminoethyl)-thiomethyl]-imidiazole sulfuric acid solution was obtained at a discharge rate of 224 g/hr. Two hundred (200) g of this aqueous solution was concentrated and thrown into 350 g of 1-propanol. The precipitate consequently produced was separated by filtration and thend dried, to afford 55 g of white crystals of 4-methyl-5-[(2-aminoethyl)-thiomethyl]-imidazole sulfuric acid.

Separately, the outer liquid obtained in the electrodialytic device 10 was withdrawn at a flow rate of 1,488 g/hr through a conduit 13 and supplied to a concentrator 14 and concentrated therein, to prepare a liquid cntaining 10.7% by weight of 4-methyl-5-[(2-aminoethyl)-thiomethyl]-imidazole sulfuric acid, 10.4% by weight of ½ sulfuric acid of 4-methylimidzole, and the balance of unaltered reactants and sulfuric acid. This liquid was returned at a flow rate of 633 g/hr through a conduit 15 to the reactor 6.

EXAMPLE 6

In 811 g of an 36 wt % hydrochloric acid, 164 g of 4-methylimidazole, and 250 g of thiazolidine were dissolved. In an autoclave, the resultant mixture was heated and stirred at 140° C. for 3 hours. In 1,225 g of the resultant reaction solution, there were contained 244 g of 4-methyl-5-[(2-aminoethyl)-thiomethyl]-imidazole dihydrochloride, 118 g of 4-methylimidazole hydrochloride, and other unaltered reactants and hydrochloric acid, indicating that the conversion of 4-methylimidazole was 50%.

Then, the reactant solution as an inner liquid and 1,000 g of water as an outer liquid were treated with an electrolytic device using ion-exchange membranes (produced by Asahi Chemical Industry Co., Ltd. and marketed under product code of "AC-110"), with an aqueous 50% sodium sulfuric acid solution used as an electrode liquid. During the course of the electrodialysis, the outer liquid was displaced with 1,000 g of water to continue the electrodialysis further.

Finally, 582 g of a liquid containing 172 g of 4-methyl-5-[(2-aminoethyl)-thiomethyl]-imidazole dihydrochloride and 410 g of water was obtained as the inner liquid. At the same time, 2,634 g of a liquid containing 72 g of 4-methyl-5-[(2-aminoethyl)-thiomethyl]-imidazole dihydrochloride, 118 g of 4-methylimidazole hydrochloride, and other unaltered reactants and hydrochloric acid was obtained as the outer liquid.

The inner liquid thus obtained was concentrated under a vacuum and thrown into 1-propyl alcohol. The crystals consequently precipitated were separated by filtration and dried, to produce 162 g of white crystals of 4-methyl-5-[(2-aminoethyl)-thiomethyl]-imidazole dihydrochloride.

EXAMPLE 7

The outer liquid obtained in Example 6 was concentrated under a vacuum to 1,010 g. In an autoclave, the concentrate and 57 g of 4-methylimidazole, and 71 g of an aqueous 36 wt % hydrochloride acid solution added thereto were heated for reaction at 140° C. for 2 hours. The resultant reaction solution contained 243 g of 4-methyl-5-[(2-aminoethyl)-thiomethyl]-imidazole dihydrochloride, 119 g of 4-methylimidazole hydrochloride, other unaltered reactants, and hydrochloric acid, representing the same composition as the reaction solution of the first cycle of reaction. When this reaction solution was subject to electrodialysis in the same manner as in Example 6, there was obtained 450 g of an inner liquid containing 170 g of 4-methyl-5-[(2-aminoethyl)-thiomethyl]-imidazole dihydrochloride and the balance of water.

The outer liquid was concentrated under a vacuum and then recycled to the next cycle of reaction.

EXAMPLE 8

In an apparatus constructed as illustrated in FIG. 1, 38 wt % hydrochloric acid was supplied at a flow rate of 6.75/min. through a conduit 1, 4-methylimidazole at a flow rate of 5.75 g/min. through a conduit 2, thiazolidine hydrochloride at a flow rate of 8.8 g/min. through a conduit 3 respectively into a mixing tank 4. The resultant mixture was supplied at a flow rate of 21.3 g/min from the mixing tank 4 through a conduit 5 to a reactor 6 kept at 140° C.

The retention time of the reaction solution in the reactor 6 was 2 hours and 30 minutes. From the reactor 6, the resultant reaciton solution was continuously withdrawn at a flow rate of 162 g/min. through a conduit 7. This reaction solution contained 15.1% by weight of 4-methyl-5-[(2-aminoethyl)-thiomethyl]-imidazole dihydrochloride, 7.3% by weight of 4-methylimidazole hydrochloride, and the balance of unaltered reactants and hydrochloric acid, indicating that the conversion of 4-methylimidazole was 50%. This reaction solution was placed in a condenser 8 and cooled therein to below 50° C. and was supplied through a conduit 9 as an inner liquid to an electrodialytic device using ion-exchange membranes (produced by Asahi Chemical Industry Co., Ltd. and marketed under product code of "AC-110"), with an aqueous 5% sodium sulfuric acid solution used as an electrode liquid. Through a conduit 11, water was supplied as an outer liquid to the electrodialytic device at a flow rate of 272 g/min. Through a conduit 12, an aqueous 17.44 wt % 4-methyl-5-[(2-aminoethyl)-thiomethyl]-imidazole dichloride solution was obtained at a discharge rate of 98 g/min.

Five hundred and eighty two (582) g of this aqueous solution was concentrated and thrown into 1,000 g of 1-propanol. The precipitate consequently produced was separated by filtration and then dried, to afford 162 g of white crystals of 4-methyl-5-[(2-aminoethyl)-thiomethyl]-imidazole dihydrochloride.

Separately, the outer liquid obtained in the electrodialytic device 10 was withdrawn at a flow rate of 336.3 g/min. through a conduit 13 and supplied to a concentrator 14 and concentrated therein, to prepare a liquid containing 5.2% by weight of 4-methyl-5-[(2-aminoethyl)-thiomethyl]-imidazole dihydrochloride, 8.4% by weight of 4-methylimidazole hydrochloride, and the balance of unaltered reactants and hydrochloric acid. This liquid was returned at a flow rate of 141 g/min. through a conduit 15 to the reactor 6.

REFERENTIAL EXAMPLE 3

Synthesis of formaldehyde adduct of cysteamine

An aqueous solution of adduct of cysteamine with formaldehyde was obtained by adding 302 g of aqueous 75 wt % cysteamine hydrochloride solution into 162 g of an aqueous 37 wt % formaldehyde solution.

EXAMPLE 9

In 811 g of 36 wt % hydrochloric acid, 164 g of 4-methylmidazole, and 464 g of the adduct of cysteamine obtained in Referential Example 3 were dissolved. In an autocalve, the resultant mixture was heated and stirred at 140° C. for 2 hours. In 1,439 g of the resultant reaction solution, there were contained 244 g of the 4-methyl-5-[(2-aminoethyl)-thiomethyl]- imidazole dihydrochloride, 18 g of 4-methylimidazole hydrochloride, and other unaltered reactants and hydrochloric acid, indicating that the conversion of 4-methylimidazole was 50%.

Then, the reaction solution as an inner liquid and 1,000 g of water as an outer liquid were treated with an electrolytic device using ion-exchange membranes (produced by Asahi Chemical Industry Co., Ltd. and marketed under product code of "AC-110"), with an aqueous 50% sodium sulfuric acid solution used as an electrode liquid. During the course of the electrodialysis, the outer liquid was displaced with 1,000 g of water to continue the electrodialysis further.

Finally, 794 g of a liquid containing 170 g of 4-methyl-5-[(2-aminoethyl)-thiomethyl]-imidazole dihydrochloride and 624 g of water was obtained as the inner liquid. At the same time, 2,640 g of a liquid containing 74 g of 4-methyl-5-[(2-aminoethyl)-thiomethyl]-imidazole hydrochloride, and other unaltered reactants and hydrochloric acid was obtained as the outer liquid.

The inner liquis thus obtained was concentrated under a vacuum and thrown into 1-propanol. The crystals consequently precipitated were separated by filtration and dried, to produce 159 g of white crystals of 4-methyl-5-[(2-aminoethyl)-thiomethyl]-imidazole dihydrochloride

EXAMPLE 10

The outer liquid obtained in Example 9 was concentrated under a vacuum to 1,000 g. In an autoclave, the concentrate and 56 g of 4-methylimidazole and 70 g of 36 wt % hydrochloric acid added thereto were heated for reaction at 140° C. for 1 hour and 30 minutes. The resultant reaction solution contained 245 g of 4-methyl-5-[(2-aminoethyl)-thiomethyl]-imidazole dihydrochloride, 117 g of 4-methylimidazole hydrochloride, other unaltered reactants, and hydrochloric acid, representing the same composition as the reaction solution of the first cycle of reaction. When this reaction solution was subjected to electrodialysis in the same manner as in Example 9, there was obtained 255 g of an inner liquid containing 170 g of 4-methyl-5-[(2-aminoethyl)-thiomethyl]-imidazole dihydrochloride and the balance of water.

The outer liquid was concentrated under a vacuum and then recycled to the next cycle of reaction.

EXAMPLE 11

In an apparatus constructed as illustrated in FIG. 2, an aqueous 75 wt % cysteamine solution was supplied at flow rate of 90.8 g/h through a conduit 1, and an aqueous 37 wt % formaldehyde solution was supplied at a flow rate of 48.7 g/hr through a conduit 3 respectively into a mixing tank 4. The resultant mixture was supplied from the mixing tank 4 through a conduit 5 to a reactor 6.

The reactor was kept at 140° C. and the retention time of the reaction solution in the reatator 6 was controlled to be 2 hours. From the reactor 6, the resultant reaciton solution was continuously withdrawn at a flow rate of 1,397 g/hr through a conduit 7 and then cooled to below 50° C. through a condenser 8. This reaction solution contained 17.46% by weight of 4-methyl-5-[(2-aminoethyl)-thiomethyl]-imidazole dihydrochloride, 8.4% by weight of 4-methylimidazole hydrochloride, and the balance of unaltered reactants and hydrochloric acid, indicating that the conversion of 4-methylimidazole was 50%. This reaction solution was supplied through a conduit 9 as an inner liquid to an electrodialytic device using io-exchange membranes (produced by Asahi Chemical Industry Co., Ltd. and marketed under product code "AC-110"), with an aqueous 5% sodium sulfuric acid solution used as an electrode liquid. Through a conduit 11, water was supplied as an outer liquid to the electrodialytic device at a flow rate of 2,341 g/hr. Through a conduit 12, an aqueous 20.1 wt % 4-methyl-5-[(2-aminoethyl)-thiomethyl]-imidazole dihydrochloride solution was obtained at a discharge rate of 721 g/hr.

Separately, the outer liquid obtained in the electrodialytic device 10 was withdrawn at a flow rate of 3,017 g/hr through a conduit 13 and supplied to a concentrator 14 and concentrated therein, to prepare a liquid containing 6.71% by weight of 4-methyl-5-[(2-aminoethyl)-thiomethyl]-imidazole dihydrochloride, 8.15% by weight of 4-mtehylimidazole hydrochloride, and the balance of unaltered reactants and hydrochloric acid. This liquid was returned at a flow rate of 1,454 g/hr through a conduit 15 to the reactor 6.

One hundred (100) g of this aqueous solution was concentrated and thrown into 150 g of 1-propanol. The precipitate consequently produced was separated by filtration and then dried, to afford 19 g of white crystals of 4-methyl-5-[(2-aminoethyl)-thiomethyl]-imidazole dihydrochloride.

EXAMPLE 12 AND COMPARATIVE EXAMPLE

Varying conversion of raw material 4-methylimidazole in the procedure of Example 11, variation of selectivity of produced 4-methyl-5-[(2-aminoethyl)-thiomethyl]-imidazole was determined and a curve A shown in FIG. 3 was obtained.

On the other hand, relationship between conversion of 4-methyl imidazole and selectivity of 4-methyl-5-[(2-aminoethyl)-thiomethyl]-imidazole in a method comprising causing 4-methyl imidazole, cysteamine and formaldehyde to react at the same time in a concentrated hydrochloric acid gave a curve B in FIG. 3.

What is claimed is:

1. A method for the production of 4-methyl-5-[(2-aminoethyl)-thiomethyl]-imidazole comprising causing 4-methylimidazole or a salt thereof to react with at least one member selected from the group consisting of (a) a formaldehyde adduct of cysteamine, (b) 2-aminoethanethiol sulfuric acid and formaldehyde or a formaladehyde oligomer, and (c) thiazolidine or a salt thereof, in the presence of a mineral acid, removing a portion of reaction liquid out of the reaction system while maintaining molar concentration of 4-methyl-5-[(2-aminoethyl)-thiomethyl]-imidazole in the reaction system not exceeding 70 mol % based on total mol numbers of 4-methylimidazole and 4-methyl-5-[(2-aminoethyl)-thiomethyl]-imidazole, then separating a liquid containing 4-methyl-5-[(2-aminoethyl)-thiomethyl]-imidazole from the removed portion of reaction liquid, and recycling the remainder into the reaction system.

2. A method according to claim 1, wherein said mineral acid is used in the form of an aqueous solution containing said mineral acid in a concentration in the range of 10 to 70% by weight.

3. A method according to claim 1, wherein said reaction is carried out at a temperature in the range of 100° to 180° C.

4. A method according to claim 1, wherein said separation is effected by an electrodialytic technique.

5. A method according to claim 1, wherein the molar ratio of 4-methylimidazole or salt thereof to at least one member selected from the group consisting of (a) formaldehyde adduct of cysteamine, (b) 2-aminoethanethiol sulfuric acid and formaldehyde or oligomer thereof, and (c) triazolidine or a salt thereof and is in the range of 1:0.9–1.1.

6. A method according to claim 1, wherein said concentration is maintained in the range of 40 to 60 mol %.

7. A method for the production of 4-methyl-5-[(2-aminoethyl)-thiomethyl]-imidazole comprising causing 4-methylimidazole or a salt thereof to react with a formaldehyde adduct of cysteamine in the presence of a mineral acid, removing a portion of a reaction liquid out of the reaction system while maintaining molar concentration of 4-methyl-5-[(2-aminoethyl)-thiomethyl]-imidazole in the reaction system not exceeding 70 mol % based on total mol numbers of 4-methylimidazole and 4-methyl-5-[(2-aminoethyl)-thiomethyl]-imidazole, then separating a liquid containing 4-methyl-5-[(2-aminoethyl)-thiomethyl]-imidazole from the removed portion of reaction liquid, and recycling the remainder into the reaction system.

8. A method according to claim 7, wherein said mineral acid is used in the form of an aqueous solution containing said mineral acid in a concentration in the range of 10 to 70% by weight.

9. A method according to claim 7, wherein said reaction is carried out at a temperature in the range of 100° to 180° C.

10. A method according to claim 7, wherein the molar ratio of 4-methylimidazole and the formaldehyde adduct of cysteamine is in the range of 1:0.9–1.1.

11. A method according to claim 7, wherein said separation is effected by an electrodialytic technique.

* * * * *